United States Patent [19]

Puricelli

[11] Patent Number: 5,215,973
[45] Date of Patent: Jun. 1, 1993

[54] OPTICALLY ACTIVE AND RACEMIC HYDRATED DIACETYLESTERS OF α-GLYCERO-PHOSPHORYL-CHOLINE

[75] Inventor: Laura Puricelli, Brescia, Italy

[73] Assignee: Magis Farmaceutici S.p.A., Brescia, Italy

[21] Appl. No.: 840,095

[22] Filed: Feb. 24, 1992

[30] Foreign Application Priority Data

| Mar. 7, 1991 | [IT] | Italy | MI 91A000590 |
| Apr. 18, 1991 | [IT] | Italy | MI 91A001069 |
| Apr. 18, 1991 | [IT] | Italy | MI 91A001070 |
| May 17, 1991 | [IT] | Italy | MI 91A001369 |

[51] Int. Cl.$^5$ .................... A61K 31/685; C07F 9/10
[52] U.S. Cl. ....................................... 514/78; 558/169
[58] Field of Search ........................ 558/169; 514/78

[56] References Cited

U.S. PATENT DOCUMENTS

| 3,687,932 | 8/1972 | Nakamachi et al. | 536/29 |
| 4,607,046 | 8/1986 | Morita et al. | 514/399 |

FOREIGN PATENT DOCUMENTS

0329053 8/1989 European Pat. Off. .
63-139187 10/1988 Japan .

OTHER PUBLICATIONS

Robert H. Pearson, "The Molecular Structure of Lecithin Dihydrate", *Nature* vol. 281 pp. 499–501, 1987.
N. H. Phuong, et al. "Chimie Organique". *C.R. Acad. Sc. Paris* vol. 283, pp. 323–325, 1976.
N. H. Phuong, et al. "Chimie Organique". *C.R. Acad. Sc. Paris* vol. 283, pp. 229–231, 1976.
Etsuo Hasegawa, et al. "A Convenient Synthesis of Mixed-Acid Glycerophosphocholines". *Journal of Synthetic Organic Chemistry* No. 1, pp. 60–62, 1986.

*Primary Examiner*—Mary C. Lee
*Assistant Examiner*—Michael G. Ambrose
*Attorney, Agent, or Firm*—Stevens, Davis, Miller & Mosher

[57] ABSTRACT

Monohydrate 1,2-di-O-acetyl-glycero-phosphoryl-choline in optically active and racemic form, processes for their preparation and pharmaceutical compositions containing them as the active principle for treating cerebral involutions of the aged and for treating dislipidemia and hyperlipoproteinemia.

24 Claims, No Drawings

OPTICALLY ACTIVE AND RACEMIC HYDRATED DIACETYLESTERS OF α-GLYCERO-PHOSPHORYL-CHOLINE

The present invention relates to optically active and racemic mixtures of monohydrate 1,2-di-O-acetyl-glycero-3-phosphoryl-choline, their methods of preparation and pharmaceutical compositions containing them for treating the cerebral involution syndromes of the aged, dyslipidemia, and hyperlipoproteinemia. This compound in the anhydrous form is a highly hygroscopic paste. This creates considerable problems when it is used to prepare pharmaceutical formulations. The Applicant has now found that the hydrated form of both the individual optically active isomer and of the raceme of 1,2-di-O-acetyl-glycero-3-phosphoryl-choline is a flowable, stable and non hygroscopic crystalline powder with a well defined melting point between 99° and 101° C., which products can be therefore used more easily than the corresponding anhydrous products, to obtain more stable pharmaceutical formulations. Specifically, the compounds of the present invention are the optically active isomers or the raceme of 1,2-di-O-acetyl-glycero-3-phosphoryl-choline monohydrate, whose structural formula can be represented in the following manner:

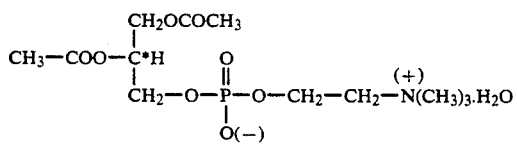

wherein the asterisk indicates the presence of an asymmetric carbon.

The present invention also provides pharmaceutical compositions comprising a therapeutically effective amount of the compound of formula (I) suitably combined with excipients, vehicles and/or solvents conventionally used for preparing pharmaceutical formulations. The pharmaceutical compositions according to the present invention are particular advantageous for treating cerebral involutions of the aged and for treating dislipidemia and hyperlipoproteinemia. The pharmaceutical compositions of the present invention are, in particular, suitable for oral and parenteral administration. Object of the present invention are also processes for preparing the compound of formula (I). For example 1,2-di-O-acetyl-glycero-phosphoryl-choline may be obtained according to the following process which comprises treating the corresponding anhydrous form with water until it contains from 5 to 10%, preferably 7%, by weight of water, followed by crystallization from an organic solvent of medium polarity, preferably alcohols, such as isopropylalcohol, or a mixture of an alcohol and a ketone, as for example absolute ethanol and acetone. The treatment with water in said process can be obtained (i) by treating the anhydrous 1,2-di-O-acetyl-glycero-phosphoryl-choline with the above mentioned polar solvent or (ii) by directly treating the anhydrous 1,2-di-O-acetyl-glycero-phosphoryl-choline with one of the polar solvents mentioned above, containing a small quantity of water and then crystallizing the hydrated form from the same solvent. For preparing the optically active form L, the above mentioned process encompasses the use of L-1,2-di-O-acetyl-glycero-phosphoryl-choline, which is obtained in turn by acetylating L-α-glycero-phosphoryl-choline. The product may be obtained by the process described in EP217765, by using either deoiled soya or egg lecithins as the starting material, and by deacylating with metal alkoxides, and complexing the resulting mixture of L-α-glycero-phosphoryl-ethanolamine and L-α-glycero-phosphoryl-choline with zinc halide, decomposing the complexes by means of an organic base, purifying and separating L-α-glycero-phosphoryl-choline from L-α-glycero-phosphoryl-ethanolamine by means of an ion exchange resin. This process presents considerable disadvantages, including that it requires significant quantities of solvents, a long time, and it gives a very impure L-α-glycero-phosphoryl-choline in a low yield, because it is difficult to remove L-α-glycero-phosphoryl-ethanolamine by eluting the raw product on a chromatographic column. The Applicant has therefore also found new processes selective for preparing the L-form, not requiring the use as the starting material of L-α-glycero-phosphoryl-choline, derived from natural products. The monohydrate L-1,2-di-O-acetyl-glycero-phosphoryl-choline may be obtained according to a process comprising the following steps:

a) 2-chloro-2-oxa-1,3,2-dioxaphospholane of formula (II)

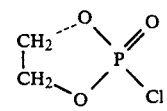

is condensed with L-1,2-di-O-acetylglycerol of formula (III)

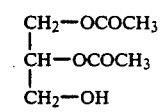

in an apolar solvent, preferably an ether, more preferably ethyl ether, preferably at room temperature in the presence of triethylamine, thereby obtaining the intermediate of formula (IV)

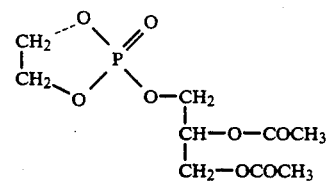

b) the intermediate of formula (IV) is reacted with an excess of trimethylamine under pressure, preferably at 1.5 atmospheres and at 50° C., thereby obtaining anhydrous raw L-1,2-di-O-acetylglycero-phosphoryl-choline;

c') the raw product obtained in (b) is then dissolved in an alcoholic solvent, preferably methanol, filtered on carbon and concentrated to a small volume under vacuum, afterwards it is eluted on a cationic exchange resin, preferably an Amberlite IR 120 (H+) type resin, by using as the eluent a hydroalcoholic solution, preferably aqueous methanol; the eluted product obtained is treated according to one of the following operating conditions: (i) it is concentrated under vacuum until containing a water amount ranging from 5 to 10%, preferably 7% by weight, and then crystallized from a mixture of a ketone and an alcohol, preferably acetone and absolute ethanol in a volumetric ratio 10:1; or (ii) it is completely evaporated until obtaining a residue, which is directly crystallized from an alcoholic solvent, preferably methanol, containing 3% by weight of water; or c") the raw product obtained in step (b) is separated from the reaction mixture by elution on a chromatographic column, by using as the eluent the following solvents or mixture of solvents in sequence: chloroform, choloroform-methanol in the following volumetric ratio: 100:2, 100:7, 4:1, 1:1, the product thus purified is treated with carbon in a polar solvent, preferably methanol, in order to remove any color, and the solvent is completely removed, thereby obtaining pure anhydrous L-α-diacetylglycerophosphorylcholine, which is converted into the monohydrate form according to one of the following alternative operating conditions: (i') by treating the anhydrous form with from 5 to 10%, preferably 7% by weight of water, and crystallizing the hydrated form from a polar solvent, preferably methanol, or a mixture of polar solvents; or (ii') treating directly the purified anhydrous form with a polar solvent, preferably methanol, containing a small amount, preferably 3%, of water, and crystallizing the monohydrate form from the same solvent. The crystallization of the hydrated form described in step (c') or (c") preferably occurs at temperatures lower than 0° C., preferably −20° C. A further process for preparing monohydrated L-1,2-di-O-acetyl-glycero-phosphoryl-choline comprises the following steps:

a) reacting the choline phosphate salt of formula (V):

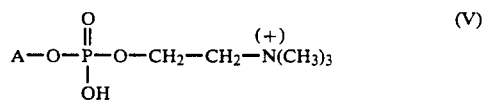
(V)

wherein A is a cation selected from: Li+, Na+, K+, or N(+)(CH3)4 with the optically active form D of the compound of formula (VI)

(VI)

wherein X is selected from Cl, Br, I, and O-tosyl, Y is —COCH3, or the Y groups together form a

groups. in polar solvents, preferably alcoholic solvents such as methanol, absolute ethanol, apolar solvents selected from ethereal solvents such as diglyme, dioxane, tetrahydrofuran, and other apolar solvents such as methylcellosolve acetate, or a mixture of both polar and apolar solvents optionally in the presence of alkylating adjuvants and solubilizers specific for the cations such as crown ethers;
thereby obtaining the intermediate of formula (VII):

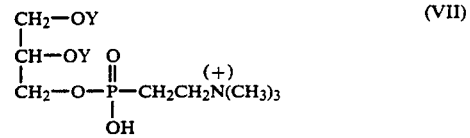
(VII)

b) in the case where the Y groups form together a

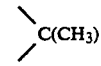

group hydrolizing the acetalic group of the compound (VII) in a mineral acid such as a hydrochloric acid aqueous solution at pH 2,3, or organic acid such as glacial acetic acid thereby obtaining L-α-glycero-phosphoryl-choline;

c) reacting L-α-glycero-phosphoryl-choline from step (b) with a mixture of acetic anhydride and pyridine respectively in molar ratio 3:2 in the presence of glacial acetic acid as the solvent, thereby obtaining anhydrous L-1,2-di-O-acetyl-glycero-phosphoryl-choline;

d) eluting the anhydrous L-1,2-di-O-acetyl-glycerophosphoryl-choline, coming from step (a) (in case the substituents Y in formula (VII) are —COCH3), or coming from step (c) on a cationic exchange resin, preferably an Amberlite type resin IR 120(H+) using as the eluent an aqueous alcoholic solvent, preferably methanol, then concentrating the eluted product until it contains an amount of water ranging from 2 to 10% by weight, more preferably from 3 to 7%.

In particular, in the process according to the present invention, when the reactant of formula (V) has A=Na, the reactant of formula (VI) has X=Br and the substituents Y form together the group

the reaction described in step (a) is carried out in methanol at the reflux temperature, and the molar ratio of the two reactants is respectively of 2:1;
step (b) is carried out in the presence of hydrochloric aqueous solution having a pH 2.3.

When in the above mentioned process the reactant of formula (V) having A=Li+, K+, N(+)(CH3)4, and the reactant of formula (VI) in which the substituents Y forming

and X=O-tosyl, are used, step (a) is carried out in absolute ethanol, in the presence of crown ethers specific for the cation at temperatures ranging from 50° to 70° C.;
step (b) is carried out in the presence of hydrochloric acid 1N, and the reaction temperature is ≦40° C.

When in the above mentioned process the reactant of formula (VI) is used having Y=—COCH3 and X=Br or —O-tosyl, step (a) is carried out in the presence of a mixture of THF and isopropanol.

The intermediate of formula (VI) having X=Br, and the substituents Y forming together

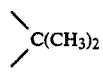

is a product commercially available with the name D-3-bromo-solketal. The compound of formula (VI) having X=O-tosyl and the substituents Y forming together

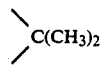

is obtained by reacting the 1,2 isopropylidene glycerol of formula (VIII):

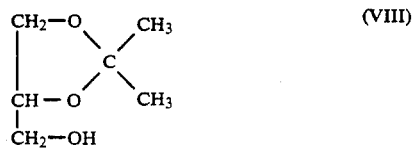

with para-toluen-sulphonyl-chloride in the presence of a hydrochloric acid acceptor, preferably pyridine, at 0° C.

The choline phosphate salt of formula (V) is obtained by reacting the choline phosphate acid with the corresponding hydroxide. The following examples are reported for illustrative, but not limitative purposes.

EXAMPLE 1

180 ml of acetone and 20 ml of ethanol are added to 51 g of (+) 1,2-di-O-acetyl-glycero-3-phosphoryl-choline which has previously been made to absorb water in a quantity of 7% by weight. The mixture is stirred under reflux until a complete solution has formed. The solution is left to crystallize at ambient temperature, and the precipitate obtained is filtered off and dried until it reaches constant weight. Forty-two grams of a white solid are obtained having the following characerics:

|  | Elemental analysis: | | | |
| --- | --- | --- | --- | --- |
|  | C | H | N | P |
| calculated (%): | 40.10 | 7.29 | 3.90 | 8.62 |
| found (%): | 39.9 | 7.2 | 4.0 | 8.7 |
| M.P. | 99-100° C. | | | |
| H$_2$O K.F. | 5.8% | | | |
| [α]$^{20}$s.s | +7.7 (c = 10, water) | | | |

EXAMPLE 2

95 ml of isopropyl alcohol are added to 10 g of (+) 1,2-di-O-acetyl-glycero-3-phosphoryl-choline which has previously been made to absorb water in a quantity of 7% by weight. The mixture is stirred under reflux until a complete solution has formed, which is then allowed to crystallize at ambient temperature.

After filtration and drying, 8.2 g of a white solid are obtained having the following characteristics:

| M.P. | 100-101° C. |
| --- | --- |
| H$_2$O K.F. | 7.2% |
| [α]$^{20}$s.s | +7.6 (c = 10, water) |

EXAMPLE 3

A solution consisting of 300 ml of anhydrous ether containing 46.885 g of L-1,2-diacetyl-glycerol (265 mmoles) and 26.7 g of triethylamine is added slowly under an anhydrous nitrogen stream to 950 ml of ether containing 265 mmoles of 2-chloro-2-oxa-1,3,2-dioxo-phospholan at 22° C. After two hours at the same temperature the triethylammonium chloride which forms is filtered off under nitrogen and washed with ether. The filtrate solution is evaporated and the residue (92% yield with 90% minimum purity) is left under vacuum (0.1 mm Hg) for 1 hour. The residue is cooled to 0° C. and 59.5 g of trimethylamine are added. These are reacted at about 50° C. under a pressure of 1.5 atmospheres for 3 hours. The minimum quantity of chloroform is added to the product, and the solution obtained is transferred to a 4 kg column of silicic acid in chloroform. The column is eluted with chloroform (15 liters), then with the following quantities of chloroform-methanol mixtures in the stated proportions: 15 liters of 100:2, 15 liters of 100:7, 15 liters of 7:1, 15 liters of 4:1 and 30 liters of 1:1. The latter mixture is passed until all the desired product has been eluted. The solvent is evaporated under reduced pressure and the residue is taken up in 500 ml of methanol and treated with Darco G-60 activated carbon. After filtration and evaporation, the colourless product is dissolved in 100 ml of methanol containing 3% of water, and allowed to crystallize at −20° C.

41.14 g (57% yield) of L-1,2-diacetyl-glycero-phosphoryl-choline monohydrate are obtained.

EXAMPLE 4

A solution consisting of 300 ml of anhydrous ether containing 46.885 g of L-1,2-diacetyl-glycerol (265 mmoles) and 26.7 g of triethylamine is added slowly under an anhydrous nitrogen stream to 950 ml of ether containing 265 mmoles of 2-chloro-2-oxa-1,3,2-dioxo-phospholan at 22° C. After two hours at the same temperature the triethylammonium chloride which forms is filtered off under nitrogen and washed with ether. The filtrate solution is evaporated and the residue (92% yield with 90% minimum purity) is left under vacuum (0.1 mm Hg) for 1 hour. The residue is cooled to 0° C. and 59.5 g of trimethylamine are added. These are reacted at about 50° C. under a pressure of 1.5 atmospheres for 3 hours. The mixture is concentrated by the aid of vacuum and the residue obtained is dissolved in methanol. The solution obtained is filtered on carbon, concentrated, and eluted on Amberlite resin IR 120(H+) by using as the eluent aqueous methanol. The fraction containing the product obtained is concentrated until its content of water is comprised between 5 and 10% by weight, then crystallized from a mixture of acetone:ethanol in volumetric ratio 10:1.

EXAMPLE 5

20.6 g (100 mmoles) of choline phosphate sodium salt are dissolved in 100 ml of methanol; 9.75 g (50 mmoles) of D-3-bromo-solketal were added to the solution. The mixture was heated to reflux temperature for 3 hours under stirring. Finally the mixture was cooled and the solvent was removed with the aid of vacuum. The residue thus obtained was dissolved in 15 ml of water and the pH was brought to 2.3 by means of hydrochloric acid. The mixture was heated up to two hours at 50° C. until complete hydrolysis of the protecting group consisting of acetone. The solution was eluted on a basic resin in the form of a formiate salt. The column was eluted with a gradient of concentration of formic acid and the fraction containing L-α-glycero-phosphoryl-choline was recovered. The solvent was evaporated with the aid of vacuum until obtaining a solid residue. At the end the residue was dissolved in acetone, filtered and the acetone was evaporated again; obtained were 9 g of L-α-glycero-phosphoryl-choline (yield 70%) with a minimum title: 98%. The product thus obtained was treated with a mixture of acetic anhydride:pyridine in molar ratio 3:2 respectively using glacial acetic acid as the solvent. The reaction mixture was then heated with water and eluted on Amberlite resin IR 120(H+) using as the eluent water or aqueous alcohol. The product eluted was concentrated under vacuum at T≦50%. The product obtained was then treated with water until acetic acid was completely removed. A product was obtained containing water from 5 to 10% by weight, preferably 7%. The product obtained was finally crystallized from a mixture acetone:ethanol in volumetric ratio 10:1.

EXAMPLE 6

20.6 g (100 mmoles) of sodium choline phosphate salt were suspended in 200 ml of a mixture of THF and isopropanol in volumetric ratio 1:1, 11.95 g of D-bromo 1,2-di-O-acetyl glycerol were added and 10 g of 15-crown-5. The reaction mixture was heated to 50° C. under stirring for 6 hours, following the reaction course by TLC. At the end, the solvent was evaporated and the residue obtained was dissolved in methanol and eluted on Amberlite resin IR 120 (H+). The eluate was evaporated until containing water in an amount of 7% and then crystallized from acetone:ethanol 10:1.

EXAMPLE 7

22.2 g (100 mmoles) of potassium choline phosphate salt were suspended in 200 mg of THF 10 g of 18-crown-6 and the mixture obtained was stirred for 15', thereafter 12 g (50 mmoles) of D-bromo 1,2-diacetyl-glycerol were added. The mixture was heated to 50° C. for 6 hours while maintaining a vigorous stirring and following the reaction course by TLC. At the end the solvent was evaporated and the residue was dissolved in a mixture water:methanol 1:1. The solution obtained was eluted on an Amberlite resin IR 120(H+) by using as the eluent methanol:water 1:1. The elution fraction containing the desired product was collected. The product obtained was neutralized at pH 7 and the solvent was evaporated with the aid of vacuum. The residue obtained was dissolved in absolute ethanol and filtered on carbon and the solvent was evaporated by the aid of vacuum. The residue obtained was crystallized from methanol having a content of water of 3.5% by weight.

EXAMPLE 8

Stage a-(+)-1,2-isopropylidene glycerol tosylate (III)

A solution of 6.8 g of (+)-1,2-isopropylidene-glycerol in 10 ml of pyridine cooled to 0° C. was added drop by drop to a solution of 12.95 g of p-toluene suphonyl chloride in 15 ml of the same solvent. The mixture was then left for 18 hours at 0° C. and constantly agitated, and then poured into water to dissolve the salt that had formed (pyridine chloride). The raw reaction product was extracted by using chloroform. The products extracted were washed in a diluted solution of hydrochloric acid, then with sodium bicarbonate, and lastly in water. The solvent was dried on anhydrous sodium sulphate, and then evaporated.

Stage b-Preparation of the intermediate (IV) in which A is tetramethyl ammonia 18.295 g of choline phosphate acid (IV) were dissolved in 100 ml of methanol containing 18.630 g of tetramethyl ammonium hydrate. The solvent was removed with the aid of vacuum at 40° C.

Stage c-L-α-1,2-isopropylidene-glyceryl-phosphoryl-choline (VII)

34.853 g of tetramethyl ammonium salt of phosphoryl-choline were dissolved in 300 ml of absolute alcohol. 25.43 g of (+)-1,2-isopropylidene glycerol tosylate were then added. The mixture was then heated to reflux temperature for about 18 hours. The salt was filtered and the solvent removed with the aid of vacuum.

Stage d-L-α-glyceryl-phosphoryl-choline (I)

The product obtained in the previous stage was dissolved in 100 ml of 95% ethanol and hydrolysed at 40° C. with 5 ml of hydrochloric acid 1N for one hour. The solvent was evaporated with the aid of vacuum. The residue was dissolved in 100 ml of distilled water, and the solution was then passed through an Amberlite column (IR-120-H-shape). The column was washed with 200 ml of water, the combined eluates were evaporated with the aid of a vacuum at 35° to 40° C. in the presence of phosphoric anhydride. 16.81 g of 99% pure L-α-glyceryl-phosphoryl-choline were obtained with a yield of 75%.

Stage (e) L-α-diacetylglycerophosphorylcholine monohydrate

The product thus obtained was treated with a mixture of acetic anhydride:pyridine in molar ratio 3:2 respectively using glacial acetic acid as the solvent. The reaction mixture is then heated with water and eluted on Amberlite resin IR 120(H+) using as the eluent water or aqueous alcohol. The product eluted was concentrated under vacuum at T≦50%. The product obtained was then treated with water until acetic acid was completely removed. A product was obtained containing water from 5 to 10%, preferably 7%, by weight. The product obtained was finally crystallized from a mixture of acetone:ethanol in volumetric ratio 10:1.

EXAMPLE 9

Following the same operating conditions described in example 6 monohydrate 1,2-di-O-acetyl-glycero-phosphoryl-choline was obtained by reacting D 1,2-diacetyl-3-glycerol with tetramethylammonium-choline phosphate salt.

I claim:
1. 1,2-di-O-acetyl-glycero-3-phosphoryl-choline monohydrate, in optically active or racemic form, having the following formula:

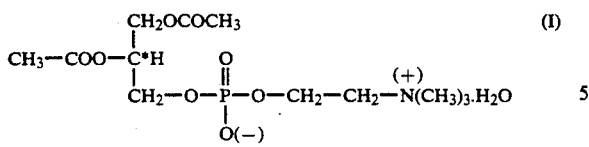

wherein the asterisk indicates the presence of an asymmetric carbon.

2. A process for preparing the compound of formula (I) in the optically active or in the racemic form

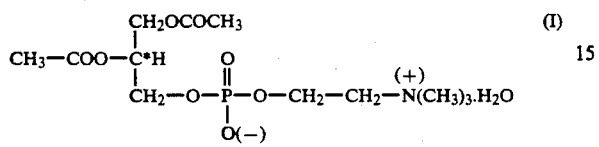

where the asterisk indicates the presence of any asymmetric carbon, the process comprising: treating the corresponding anhydrous form with water until it contains between 5 and 10% by weight of water, followed by crystallizing the compound of formula I from an organic solvent or a mixture of solvents of medium polarity.

3. The process as claimed in claim 2, characterized in that the anhydrous 1,2-di-O-acetyl-glycero-phosphoryl-choline is treated with water until it contains up to 7% by weight of water.

4. The process as claimed in claim 2, characterized in that the the organic solvent of medium polarity is an alcohol or a mixture of an alcohol and a ketone.

5. The process as claimed in claim 4, characterized in that the alcohol is isopropylalcohol.

6. The process as claimed in claim 4, characterized in that the mixture of an alcohol and a ketone is a mixture of ethanol and acetone.

7. The process as claimed in claim 2, characterized in that the treatment with water can be accomplished (i) by treating anhydrous L-1,2-di-O-acetyl-glycero-phosphoryl-choline with a small quantity of water and then crystallizing the hydrated form from a polar solvent, or (ii) treating anhydrous L-1,2-di-O-acetyl-glycero-phosphoryl-choline with a polar solvent containing a small quantity of water, and then crystallizing the hydrated form from the same solvent.

8. A process for preparing monohydrate L-1,2-diacetyl-glycero-phosphoryl-choline of formula (I)

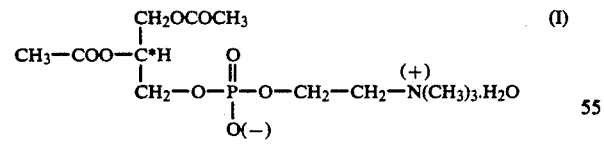

wherein the asterisk indicates the presence of an asymmetric carbon, comprising the following steps:
a) condensing 2-chloro-2-oxa-1,3,2-dioxaphospholane of formula (II):

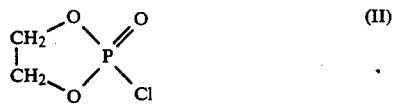

with L-1,2-di-O-acetyl-glycerol of formula (III)

in an apolar solvent, thereby obtaining the intermediate of formula (IV)

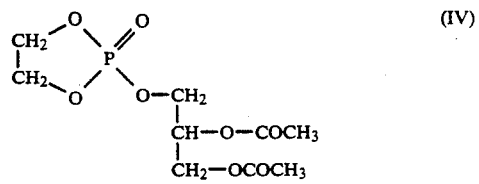

b) reacting the intermediate of formula (IV) with an excess of trimethylamine under pressure, thereby obtaining raw anhydrous L-1,2-di-O-acetyl-glycero-phosphoryl-choline;

c') the raw product obtained in (b) is then dissolved in an alcoholic solvent, filtered on carbon and concentrated to a small volume under vacuum, afterwards it is eluted on a cationic exchange resin, by using as the eluent a hydroalcoholic solution, the eluted product is treated according to one of the following operating conditions: (i) it is concentrated under vacuum until containing from 5 to 10% by weight of water then crystallized from a mixture of a keton and an alcohol; or (ii) it is completely evaporated until obtaining a residue, which is directly crystallized from an alcoholic solvent, containing 3% by weight of water; or c") the raw product coming from step (b) is separated from the reaction mixture by elution on a chromatographic column, by using as the eluent the following solvents or mixture of solvents in sequence: chloroform, choloroform-methanol in the following volumetric ratio: 100:2, 100:7, 4:1, 1:1, the product thus purified is treated with carbon in a polar solvent, in order to remove any colour, and the solvent is completely removed, thereby obtaining anhydrous L-α-diacetylglycerophosphorylcholine, which is converted into the monohydrate form according to one of the following alternative operating conditions: (i') by treating the anhydrous form with from 5 to 10% by weight of water, and crystallizing the hydrated form from a polar solvent, or a mixture of polar solvents; or (ii') treating directly the anhydrous form with a polar solvent, containing a small amount of water, and crystallizing the monohydrate form from the same solvent.

9. The process as claimed in claim 8, characterized in that the apolar solvent used in step (a) is an ether.

10. The process as claimed in claim 9, characterized in that step (a) is carried out in anhydrous ethyl ether at room temperature in the presence of triethylamine.

11. The process as claimed in claim 8 characterized in that step (b) is carried out at 1.5 atmospheres and at 50° C.

12. The process as claimed in claim 8 wherein in step c') the raw product obtained in (b) is then dissolved in methanol, filtered on carbon and concentrated to a small volume under vacuum, afterwards it is eluted on an Amberlite IR 120 (H+) type resin, by using as the eluent aqueous material; the eluted product obtained is treated according to one of the following operating conditions: (i) it is concentrated under vacuum until containing a water amount 7% by weight, and then crystallized from a mixture of acetone and absolute ethanol in a volumetric ratio 10:1; or (ii) it is completely evaporated until obtaining a residue, which is directly crystallized from methanol containing 3% by weight of water.

13. The process as claimed in claim 8 wherein in step c'') the raw product coming from step (b) is separated from the reaction mixture by elution on a chromatographic column, by using as the eluent the following solvents or mixture of solvents in sequence: chloroform, chloroform-methanol in the following volumetric ratio: 100:2, 100:7, 4:1, 1:1, the product thus purified is treated with carbon in methanol, in order to remove any color, and the solvent is completely removed, thereby obtaining anhydrous L-α-diacetylglycerophosphorylcholine, which is converted into the monohydrate form according to one of the following alternative operating conditions: (i') by treating the anhydrous form with 7% by weight of water, and crystallizing the hydrated form from methanol or a mixture of polar solvents; or (ii') treating directly the anhydrous form with methanol, containing 3% of water, and crystallizing the monohydrate form from the same solvent.

14. The process as claimed in claim 8 wherein the crystallization of the monohydrate product described in step (c') or (c'') is carried out at a temperature lower than 0° C.

15. The process as claimed in claim 14 characterized in that the hydrated product is crystallized at −20° C.

16. A process for preparing monohydrate L-1,2-di-O-acetyl-glycero-phosphoryl-chlorine of formula (I)

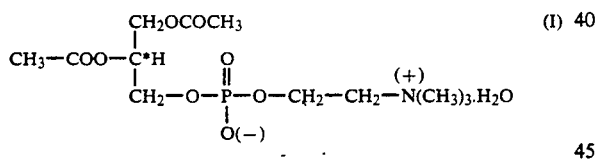

wherein the asterisk indicates the presence of an asymmetric carbon, comprising the following steps:

a) reacting the choline phosphate salt of formula (V):

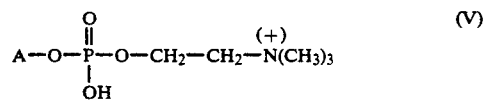

wherein A is a cation selected from: Li$^+$, Na$^+$, K$^+$, or N$^{(+)}$(CH$_3$)$_4$ with the compound of formula (VI)

wherein X is selected from Cl, Br, I, and O-tosyl, Y are —COCH$_3$ or together form a group

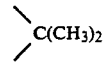

in polar solvents, selected from alcoholic solvents, apolar solvents selected from ethereal solvents and other apolar solvents, and mixture of both polar and apolar solvents optionally in the presence of alkylating adjuvants and solubilizers specific for the cations thereby obtaining the intermediate of formula (VII):

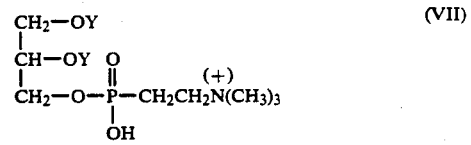

b) in case groups Y form together a group

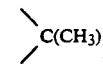

hydrolizing the acetalic group of the compound (VII) in a mineral or organic acid thereby obtaining L-α-glycero-phosphoryl-choline;

c) reacting L-α-glycero-phosphoryl-choline coming from step (b) with a mixture of acetic anhydride and pyridine respectively in molar ratio 3:2 in the presence of glacial acetic acid as the solvent, thereby obtaining anhydrous L-1,2-di-O-acetyl-glycero-phosphoryl-choline;

d) eluting the anhydrous L-1,2-di-O-acetyl-glycero-phosphoryl-choline, coming from step (a) (in case Y in formula (VII) is —COCH$_3$), or coming from step (c) on a cationic exchange resin IR 120(H$^+$) using as the eluent an aqueous alcoholic solvent, concentrating the product obtained until it contains water in amounts comprised between 2 and 10% by weight, crystallizing the product obtained after elution and concentration from a mixture of an alcohol and a ketone.

17. The process as claimed in claim 16, characterized in that step (a) is carried out in the presence of an alcoholic solvent selected from methanol, ethanol, or of an ethereal solvent selected from diglyme, dioxane, tetrahydrofuran, or in the presence of an other apolar solvent consisting of methylcellosolve acetate and in the presence of solubilizers specific for the cations consisting of crown ethers, step (b) is conducted by using as the mineral acid, hydrochloric aqueous solutions or as the organic acid, glacial acetic acid; and in step (d) the product is eluted on an Amberlite type resin IR 120(H$^+$) by using as the eluent methanol and concentrating the eluted product until it contains an amount of water ranging from 3 to 7% by weight, and crystallizing the product obtained from a mixture of ethanol and acetone.

18. The process as claimed in claim 17, characterized in that when the reactants of formula (V) having A=Na, and the reactant of formula (VI) having X=Br and the substituents Y forming together the group

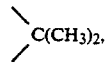

are used, the reaction described in step (a) is carried out in methanol at the reflux temperature, and the molar ratio of the two reactants is respectively of 2:1; step(b) is carried out in the presence of a hydrochloric aqueous solution having a pH 2.3.

19. The process as claimed in claim 17 characterized in that the reactant of formula (V) having $A=Li^+$, $K^+$, $N^{(+)}(CH_3)_4$ and the reactant of formula (VI) in which the substituents Y forming

and X=O-tosyl are used, step (a) is carried out in absolute ethanol, in the presence of crown ethers specific for the cation at temperatures ranging from 50° to 70° C.; step (b) is carried out in the presence of hydrochloric acid 1N, and the reaction temperature is $\leq 40°$ C.

20. The process as claimed in claim 17, characterized in that when the reactant of formula (VI) is used having $Y=-COCH_3$ and X is Br or O-tosyl, step (a) is carried out in the presence of a mixture of THF and isopropanol.

21. Pharmaceutical compositions comprising a thermapeutically effective amount of the 1,2-di-O-acetyl-glycero-phosphoryl-choline monohydrate, in optically active or racemic form, having the following formula:

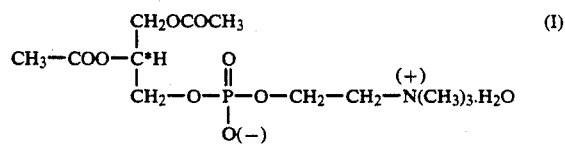

wherein the asterisk indicates the presence of an asymmetric carbon, suitably combined with excipients, vehicles and/or solvents habitually used for preparing pharmaceutical formulations.

22. The pharmaceutical compositions as claimed in claim 21 for treating cerebral involutions of the aged and for treating dislipidemia and hyperlipoproteinemia.

23. The pharmaceutical compositions as claimed in claim 21 suitable for oral and parenteral administration.

24. The pharmaceutical compositions as claimed in claim 21, characterized in that they contain L-1,2-di-O-acetyl-glycero-phosphoryl-choline monohydrate.

* * * * *